(12) United States Patent
Tsuyuki et al.

(10) Patent No.: US 7,881,423 B2
(45) Date of Patent: Feb. 1, 2011

(54) X-RAY CT APPARATUS AND X-RAY RADIOGRAPHIC METHOD

(75) Inventors: Masaharu Tsuyuki, Nasushiobara (JP); Toyoaki Tanaka, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 11/467,811

(22) Filed: Aug. 28, 2006

(65) Prior Publication Data
US 2007/0053478 A1  Mar. 8, 2007

(30) Foreign Application Priority Data
Aug. 31, 2005  (JP)  ............... 2005-252330

(51) Int. Cl.
*A61B 6/00*  (2006.01)
(52) U.S. Cl. .......................... 378/4; 378/207
(58) Field of Classification Search ............... 378/4–20, 378/901, 64, 65
See application file for complete search history.

(56) References Cited

U.S. PATENT DOCUMENTS

| | | | | |
|---|---|---|---|---|
| 4,791,934 A * | 12/1988 | Brunnett | ..................... | 600/429 |
| 5,117,829 A * | 6/1992 | Miller et al. | ................. | 600/427 |
| 5,598,453 A * | 1/1997 | Baba et al. | .................. | 378/146 |
| 5,651,043 A * | 7/1997 | Tsuyuki et al. | ............... | 378/65 |
| 5,734,692 A * | 3/1998 | Seki | ............................ | 378/65 |
| 5,754,623 A * | 5/1998 | Seki | ............................ | 378/65 |
| 6,243,439 B1 * | 6/2001 | Arai et al. | ..................... | 378/20 |
| 6,278,767 B1 * | 8/2001 | Hsieh | .......................... | 378/163 |
| 6,322,248 B1 * | 11/2001 | Yanagita et al. | ............. | 378/205 |
| 6,546,073 B1 * | 4/2003 | Lee | ............................. | 378/65 |
| 6,611,575 B1 * | 8/2003 | Alyassin et al. | ............... | 378/37 |
| 6,674,833 B2 * | 1/2004 | Shahidi et al. | ................. | 378/4 |
| 2002/0003854 A1 * | 1/2002 | Ivan et al. | ..................... | 378/20 |
| 2002/0110216 A1 * | 8/2002 | Saito et al. | .................... | 378/19 |
| 2003/0099323 A1 * | 5/2003 | Nagata et al. | .................. | 378/4 |
| 2003/0128801 A1 * | 7/2003 | Eisenberg et al. | ............. | 378/19 |
| 2004/0087850 A1 * | 5/2004 | Okerlund et al. | ............ | 600/407 |
| 2004/0161139 A1 * | 8/2004 | Samara et al. | .............. | 382/131 |
| 2004/0190674 A1 * | 9/2004 | Tsukagoshi | ..................... | 378/4 |
| 2004/0249270 A1 * | 12/2004 | Kondo et al. | ................. | 600/425 |
| 2005/0047541 A1 * | 3/2005 | Tsuyuki | ......................... | 378/4 |

FOREIGN PATENT DOCUMENTS

JP  2005-66037  3/2005

\* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

An X-ray CT apparatus is adapted for switchover between a CT mode to obtain a tomographic image of a subject and a transmission mode to obtain a transmission image of the subject, depending upon projection data acquired in an imager system thereof. The apparatus includes an image-data storage device that stores image data of the subject in a three-dimensional region, a three-dimensional image processor that performs a three-dimensional image processing on the image data and generates three-dimensional image data, for display, corresponding to a line-of-sight direction inputted from an input device, and a transmission-image generator that generates the transmission image as to the image-taking direction, from data acquired in the imager system aligned by the CPU.

22 Claims, 8 Drawing Sheets

X-RAY CT APPARATUS AND X-RAY RADIOGRAPHIC METHOD

BACKGROUND OF THE INVENTION

1. Technical Field of the Invention

The present invention relates to an X-ray CT apparatus and x-ray radiographic method that is adapted for switchover between a CT mode to obtain a tomographic image of a subject and a transmission mode to obtain a transmission image of the subject, depending upon the data acquired in the imager system thereof.

2. Description of the Related Art

The known X-ray CT (computerized tomography) apparatus, called the third generation, is oppositely arranged with an X-ray tube and an X-ray detector having a plurality of arrays of multi-channel X-ray detector elements, sandwiching a patient (subject). While rotating those through 360 degrees about the subject, an X-ray beam is irradiated from the X-ray tube to a predetermined region of the patient. The X-rays transmitted the predetermined region is measured as projection data by the X-ray detector. Based on the data, image reconstruction process is made by the use of a computer to thereby obtain a tomographic image as to the predetermined region.

In this manner, the X-ray CT apparatus usually provides nothing more than a tomographic image. However, during operation for example, there is a possible need of a transmission image on a region concerned of a subject, in addition to a tomographic image. This however requires an X-ray CT apparatus, serving also in a transmission mode, set up in an operating room.

However, the CT radiography with the existing X-ray CT apparatus tends to use an X-ray higher in intensity than that of the X-ray apparatus. The patient undergoes much exposure to X-ray radiation, thus being imposed with great burden.

Meanwhile, the X-ray apparatus having an I.I (image intensifier) requires a fine positional adjustment while actually irradiating X-rays to the patient after roughly positioning the patient relative to the apparatus. This places the patient under much exposure to X-ray radiation and hence imposes a great burden on the patient.

SUMMARY OF THE INVENTION

It is an object of the present invention to provide an X-ray CT apparatus and X-ray radiographic method that, in a transmission mode, the patient is relieved of exposure to X-ray radiation.

According to a first aspect of the invention, there is provided an X-ray CT apparatus adapted for switchover between a CT mode to obtain a tomographic image of a subject and a transmission mode to obtain a transmission image of the subject, depending upon projection data acquired in an imager system thereof, the apparatus comprising: an image-data storage device that stores image data of the subject in a three-dimensional region; a three-dimensional image processor that performs a three-dimensional image processing on the image data and generates three-dimensional image data, for display, corresponding to a line-of-sight direction inputted; a drive control that aligns the imager system depending upon an image-taking direction corresponding to the line-of-sight direction; and a transmission-image generator that generates the transmission image as to the image-taking direction, from data acquired in the imager system aligned by the drive control.

According to a second aspect of the invention, there is provided an X-ray CT apparatus adapted for switchover between a CT mode to obtain a tomographic image of a subject and a transmission mode to obtain a transmission image of the subject, depending upon projection data acquired in an imager system thereof, the apparatus comprising: an input device that inputs a tilt angle of a gantry and a tube position of an X-ray tube; a drive control that changes the tilt angle of the gantry and the tube position of the X-ray tube depending upon the tilt angle and tube position inputted by the input device; an image-data storage device that stores image data of the subject in a three-dimensional region; a three-dimensional image processor that determines an image-taking direction depending upon the tilt angle and the tube position, performs a three-dimensional image processing on the image data and generates three-dimensional image data, for display, in a line-of-sight direction corresponding to the image-taking direction; and a transmission-image generator that generates the transmission image as to the image-taking direction, from data acquired in the imager system aligned by the drive control.

According to a third aspect of the invention, there is provided an X-ray radiographic method adapted for switchover between a CT mode to obtain a tomographic image of a subject and a transmission mode to obtain a transmission image of the subject, depending upon data acquired in an imager system thereof, the method comprising: an image-data storing step that stores image data of the subject in a three-dimensional region; a three-dimensional image processing step that performs a three-dimensional image processing on the image data and generates three-dimensional image data, for display, corresponding to a line-of-sight direction inputted; a drive control step that aligns the imager system depending upon an image-taking direction corresponding to the line-of-sight direction; and a transmission-image generating step that generates the transmission image as to the image-taking direction, from data acquired in the imager system aligned by the drive control.

The X-ray CT apparatus and X-ray radiographic method, in the invention, can reduce X-ray exposure of the patient in a transmission mode.

DETAILED DESCRIPTION OF THE PREFERRED EMBODIMENTS

With reference to the accompanying drawings, description is now made on an X-ray CT apparatus and X-ray radiographic method according to embodiments of the present invention.

Figure 1:
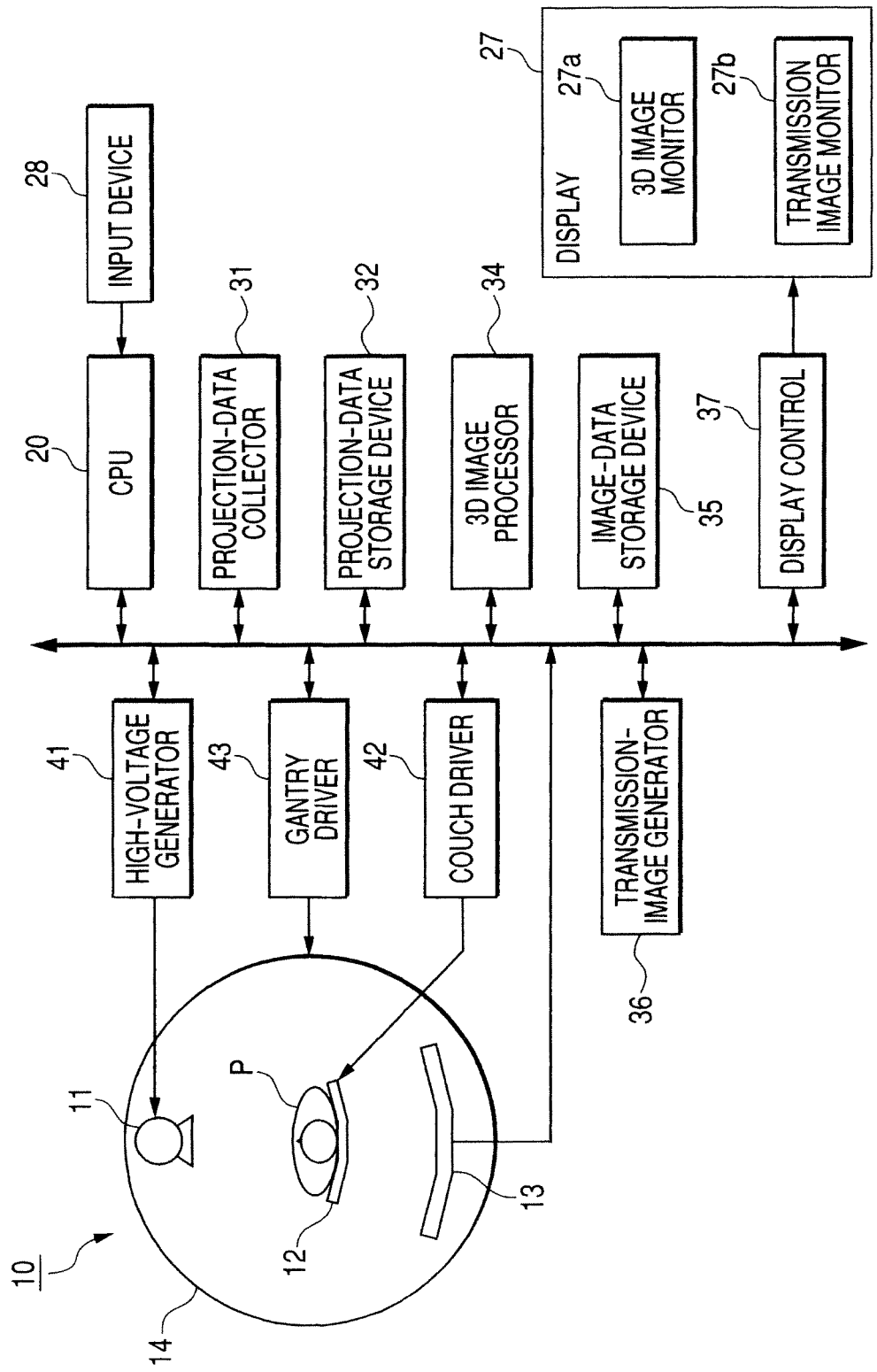
FIG. 1 is a schematic diagram showing a first embodiment of an X-ray CT apparatus according to the present invention.

FIG. 1 is a schematic diagram showing a first embodiment of an X-ray CT apparatus according to the invention.

In FIG. 1, there is illustrated an X-ray CT apparatus that can be switched over between a CT (computerized tomography) mode to obtain a tomographic image of a patient (subject) P and a transmission mode to obtain a transmission image of the patient P as on the X-ray television. The X-ray CT apparatus 10 has an imager system that includes an X-ray tube 11 to emit X-rays to the patent P, a couch plate 12 to rest the patient P thereon, an X-ray detector 13 to detect the amount of X-ray transmitted the patent P, a gantry 14 to rotate the X-ray tube 11 in unison with the X-ray detector 13.

Meanwhile, the X-ray CT apparatus 10 is also constructed based upon a computer, i.e. configured with basic hardware including a CPU (central processing unit) 20 as control means having a central role to organically control the various units constituting the X-ray CT apparatus 10, a ROM (read only memory, not shown), a RAM (random access memory, not shown), an HD (hard disk, not shown), a display 27 and an input device 28.

Furthermore, the CPU 20 reads a program stored in the HD, etc. into the X-ray CT apparatus 10. By executing the program, functions are provided as a projection-data collector 31 to gather the output of the X-ray detector 13 in the CT mode as X-ray projection data (hereinafter, referred merely to as "projection data") of the patient P at his/her slice plane, a projection-data storage device 32 to convert the projection data gathered by the projection-data collector 31 into a digital signal and store it in a memory (RAM, HD or the like), a 3D image processor 34 to generate image data (three-dimensional image data) in a three-dimensional-region from the projection data stored in the projection-data storage device 32 and perform a three-dimensional image processing on the three-dimensional image data to generate image data (3D image data) for display, an image-data storage device 35 to store, into a memory, the three-dimensional image data or 3D image data generated in the 3D image processor 34, a transmission-image generator 36 to generate a transmission image depending upon the output of the X-ray detector 13 when in a transmission mode, and a display control 37 causing to display 3D and transmission images on the monitor 27. Incidentally, the X-ray CT apparatus 10 is not limited to the arrangement to function as the sections 31, 32, 34, 35, 36 and 37, but may be configured as hardware based on a particular circuit. Otherwise, those may be combined together desirably.

The display 27 includes a 3D image monitor 27a to display, as a 3D image, the 3D image data generated in the CT mode, and a transmission-image monitor 27b to display a transmission image generated in a transmission mode.

The input device 28 includes a touch panel (not shown) to display an input content, etc. as a figure or characters or to be operated by touching a display item by the finger of an operator. Using the input device 28, the operator is allowed to input various setting values, instructions, etc. to the CPU 20. In the transmission mode, the imager system is set in position so that a transmission image can be obtained in a predetermined direction of transmission. In the position thus set up, a plurality of frame images are displayed successively to show the state of the interior of the patient P, as a moving image.

The high-voltage generator 41A provides a tube voltage and current to the X-ray tube 11, according to the instruction from the CPU 20. The tube voltage and current, in value, is suitably changed depending upon a CT mode and a transmission mode. In the CT mode, the CPU 20 controls the high-voltage generator 41 to provide a high voltage to the X-ray tube 11, under a condition of tube voltage and current suited for CT imaging, e.g. 120 kV, 300 mA. Furthermore, the CPU 20 controls the gantry driver 43 to continuously drive the gantry 14 in a predetermined direction at a proper rate, e.g. 0.5 second/rotation.

Meanwhile, in the transmission mode, the CPU 20 changes the setting on the high-voltage generator 41 to apply, to the X-ray tube 11, a tube voltage and current suited for transmission radiography, e.g. 120 kV, 100 mA. Furthermore, the CPU 20 controls the gantry driver 43 such that the gantry 14 stops from continuously rotating to position the X-ray tube 11 immediately above the patient P from which predetermined position the gantry 14 can be rotated forward or backward a predetermined angle a time.

Under the instruction from the CPU 20, the couch plate 12 is moved horizontally in an axial direction of the patient P body by the couch driver 42 (i.e. longitudinally), left and right relative to the axial direction of the body (i.e. laterally), or vertically thereof.

The X-ray detector 13 is arranged, side by side in a slice direction (axially of the patient P body), say, with 256 arrays each of which has X-ray detector elements (not shown), e.g. 800 channels, (C1-C800) matched to the spread of an X-ray beam irradiated from the X-ray tube 2, thus providing a structure compatible with so-called multi-slicing.

Under the instruction from the CPU 20, the gantry 14 is controlled by the gantry driver 43, to continuously rotate in a predetermined direction or rotate forward or reverse a desired angle a time with reference to a predetermined position. Meanwhile, the gantry 14 is controlled in its tilt angle according to the instruction from the CPU 20.

The 3D image processor 34 performs a reconstruction process to generate a CT tomographic image of a subject interior from projection data. The image-data storage device 35 stores in the memory the CT tomographic image, as three-dimensional data (e.g. volume data) that is data in a three-dimensional region. Meanwhile, the 3D image processor 34 generates 3D image data from the three-dimensional image data by three-dimensional image processing.

Here, the three-dimensional image processing, to be made at the 3D image processor 34, includes volume rendering, surface rendering, MPR (multi planar reconstruction, MIP (minimum intensity projection) and CVR (computed volume radiography).

Meanwhile, for the three-dimensional image data generated by the 3D image processor 34, attached are information of a visual point of a 3D image obtained from the relevant three-dimensional image data and a line-of-sight determined from the visual point, information of image-taking direction corresponding to the direction of the line-of-sight (projecting direction, imager system position), information of the patient and so on. The position of the imager system includes, say, the height, widthwise and longitudinal positions of the couch plate 12, the tilt angle of the gantry 14 and the tube position of the X-ray tube 11 (position at a start of transmission).

Figure 2:
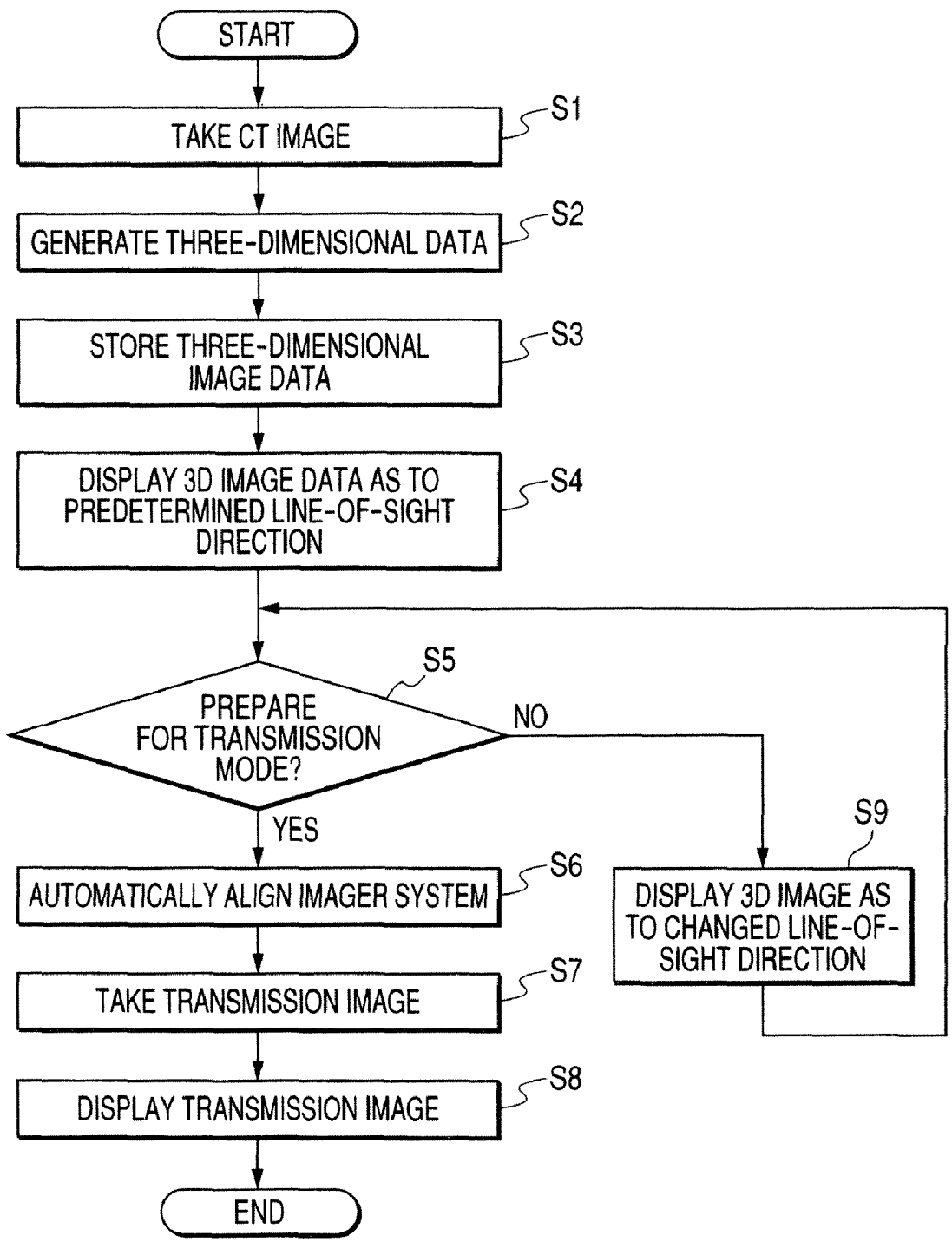
FIG. 2 is a flowchart of an X-ray radiographic method using the first embodiment of the X-ray CT apparatus.

Using a flowchart shown in FIG. 2, description is now made on a X-ray radiography with using the X-ray CT apparatus 10.

At first, CT radiography is conducted in the CT mode on the patient P resting upon the couch plate 12 for a diagnostic or remedial purpose (step S1), to collect projection data. The CPU 20 controls the high-voltage generator 41 to apply a high voltage to the X-ray tube 11 under a condition of a tube voltage and current suited for CT radiography, e.g. 120 kV, 300 mA. Furthermore, the CPU 20 controls the gantry driver 43 to continuously drive the gantry 14 in a predetermined direction at a proper rate, e.g. 0.5 second/rotation.

X-rays are irradiated from the X-ray tube 11 to the patient P. The X-rays in a portion transmitted the patient P are detected in amount by the X-ray detector 13. By the output of the X-ray detector 13, the projection-data collector 31 gathers the projection data as to the slice plane of the patient P. The projection data, gathered by the projection-data collector 31, is converted into a digital signal, which signal is stored in the memory by the projection-data storage device 32.

Based on the projection data collected in the imaging at step S1 and stored by the projection-data storage device 32, the 3D image processor 34 generates three-dimensional image data in a plurality of line-of-sight directions (step S2). For each of the three-dimensional image data generated by the 3D image processor 34, attached is the information as to the line-of-sight direction of the 3D image acquired from the three-dimensional data. The 3D image data as to the line-of-sight directions generated by the 3D image processor 34, is stored in the memory by the image-data storage device 35 (step S3).

Meanwhile, three-dimensional image processing is made on the three-dimensional image data as to a predetermined line-of-sight direction. By the display control 37, the 3D image data, for display, is displayed as a 3D image on a 3D image monitor 27a of the display 27 (step S4). Incidentally, the 3D image data may be stored in the memory by the image-data storage device 35.

Figure 3:
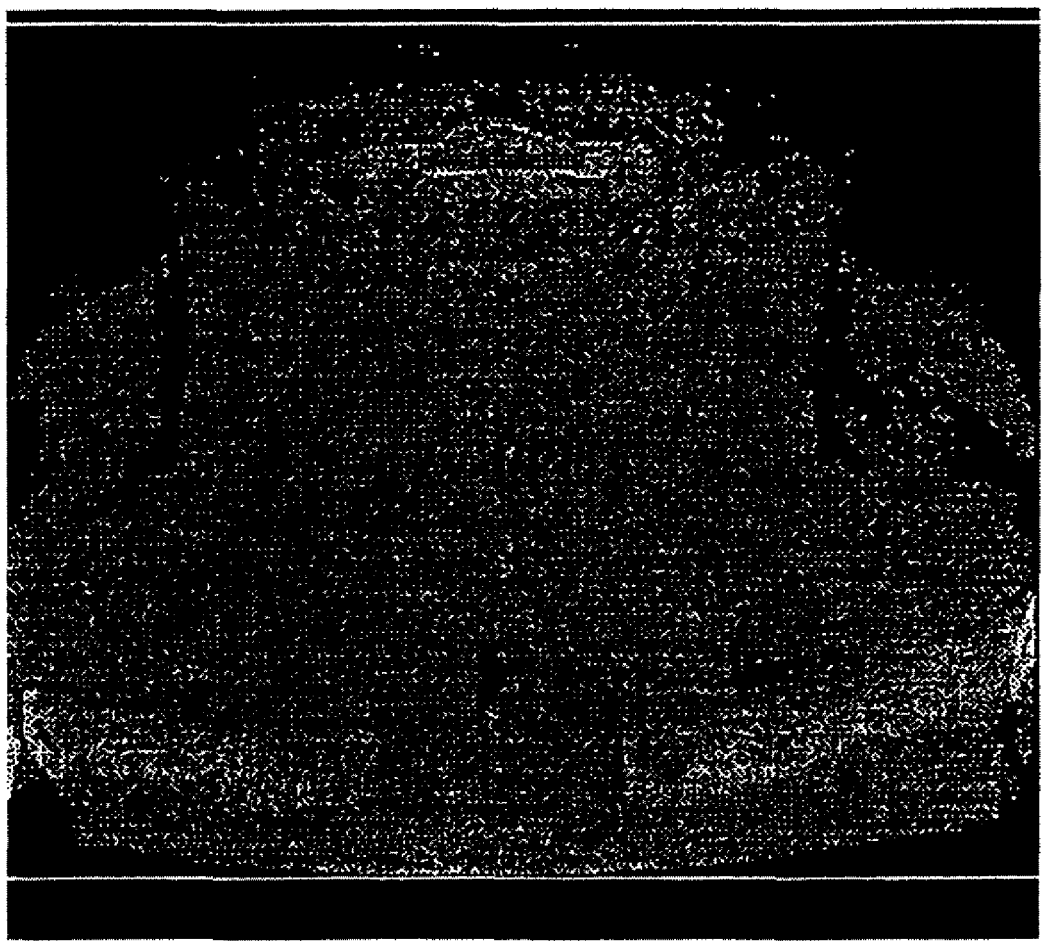
FIG. 3 is a figure showing an example of a 3D image displayed on a 3D image monitor.

FIG. 3 is a figure showing an example of a 3D image displayed on the 3D image monitor 27a. The 3D image is taken at the neck of the patient P.

Then, the operator, who is to take an image of the patient P in a transmission mode, determines whether to display a transmission image of the neck in an image-taking direction corresponding to the predetermined line-of-sight direction displayed at step S4 or to display a transmission image of the neck in an image-taking direction not corresponding to the predetermined line-of-sight direction displayed at step S4. For example, the operator determines whether to display a transmission image of the neck in the same image-taking direction as the predetermined line-of-sight direction or to display a transmission image of the neck in a different image-taking direction from the predetermined line-of-sight direction displayed at the step S4. Note that the same image-taking direction as the predetermined line-of-sight direction means substantially the same image-taking direction as the predetermined line-of-sight direction instead of perfectly the same image-taking direction as the predetermined line-of-sight direction.

Where desired to display a transmission image of the neck in the same image-taking direction as the predetermined line-of-sight direction displayed at the step S4, the operator performs a line-of-sight determining operation by use of the input device 28. Meanwhile, where desired to display a transmission image of the neck in a different image-taking direction from the predetermined line-of-sight direction displayed at the step S4, the operator performs a line-of-sight changing operation by use of the input device 28. The line-of-sight determining or changing operation using the input device 28 is to be made, say, on a screen where to set up the position of the imager system.

Figure 4:
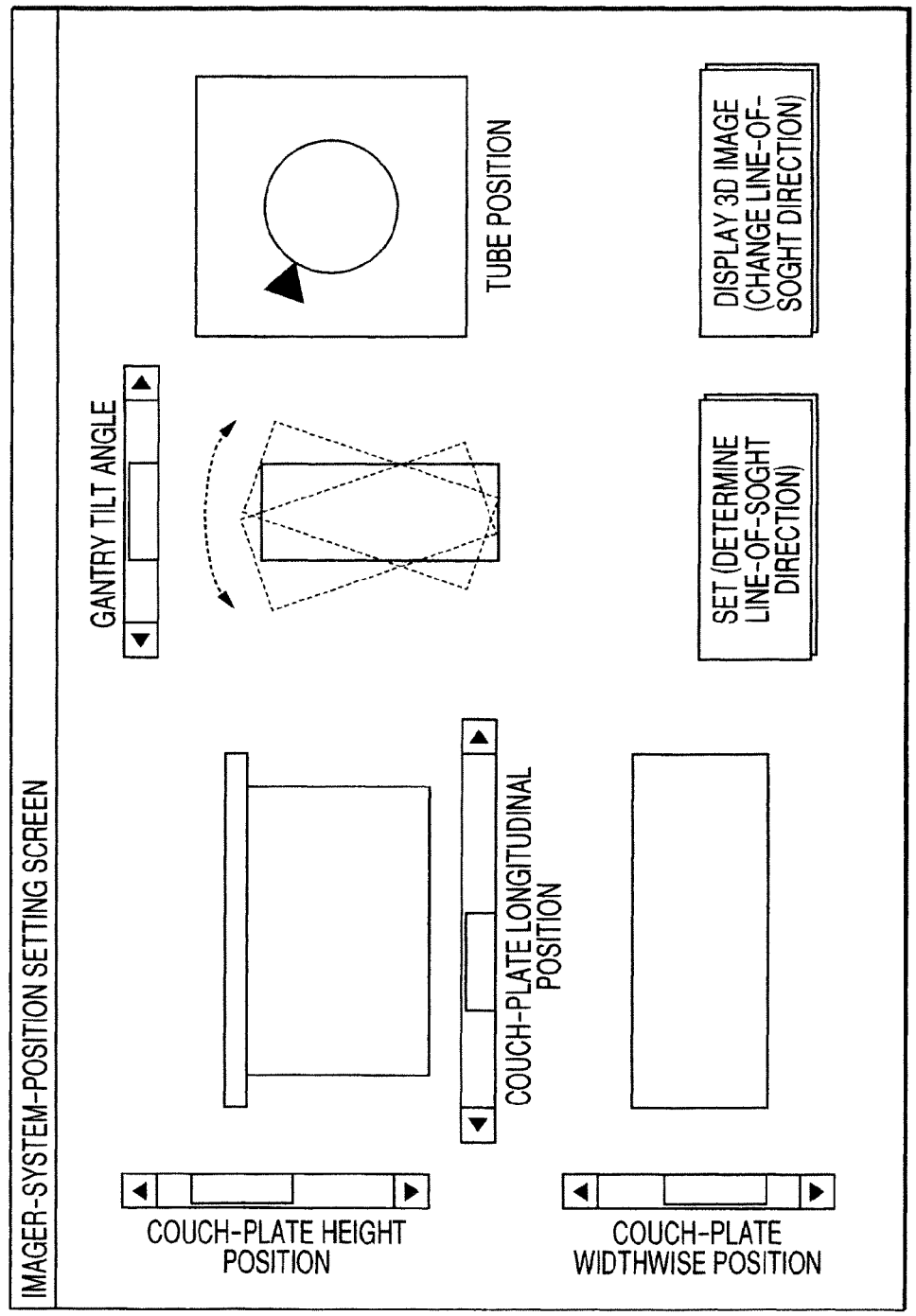
FIG. 4 is a figure showing an example of a positioning screen for the imager system.

FIG. 4 is a figure showing an example of a position-setting screen for the imager system.

On the imager-system-position setting screen shown in FIG. 4, it is possible to select height, widthwise and longitudinal (axial of the body) positions of the couch plate 12, a tilt angle of the gantry 14 and a tube position of the X-ray tube 11, as a virtual position of the imager system (on-screen position of the imager system). On the imager-system-position setting screen, the virtual position selected for imager system can be determined as a real position of the imager system.

The virtual position of the imager system, initially of display on the imager-system-position setting screen, is set up based on the same image-taking direction as the predetermined line-of-sight direction attached to the 3D image displayed at the step S4. When to perform a line-of-sight-direction determining operation on the imager-system-position setting screen, a button "Set (determine line-of-sight-direction)" is clicked. Clicking the button "Set" determines an imager-system virtual position where to perform a transmission in the same image-taking direction as the predetermined line-of-sight direction of the 3D image displayed at the step S4.

Furthermore, on the imager-system-position setting screen, it is possible to perform a line-of-sight direction changing operation on the 3D image displayed at the step S4. In performing, on the imager-system-position setting screen, a line-of-sight direction changing operation to change the line-of-sight direction of the 3D image displayed at the step S4, the operator desirably moves the imager-system virtual position by the utilization of a moving device provided on the imager-system-position setting screen. The operator is allowed to change the height, widthwise and longitudinal positions of the couch plate 12 as the virtual position of the image system and the tilt angle of the gantry 14 by moving a scroll bar, or moving device, to a desired position. Meanwhile, the operator puts the cursor on a tube mark "□", or moving device, and then drags the tube mark up to a desired point on a path. After desirably moved the virtual position of the imager system, clicked is the button "Display 3D Image (line-of-sight direction change)".

Incidentally, the moving device provided on the imager-system-position setting screen may be of a numeral (angle, etc.) representative of a tilt angle of the gantry 14 and a tube position of the X-ray tube 11, as a virtual position of the imager system. When changing the numeral representing the tilt angle of the gantry 14 and tube position of the X-ray tube 11, numerical input is made on the input device 28. The moving device, provided on the imager-system-position setting screen, may include a numeral (distance) representative of at least one of the height, widthwise and longitudinal positions of the couch plate 12 in addition to the tilt angle of the gantry 14 and tube position of the X-ray tube 11.

Meanwhile, the moving device may be hardware, such as a slider, provided outside the imager-system-position setting screen and for changing the height, widthwise and longitudinal positions of the couch plate 12 and tilt angle of the gantry 14, or hardware, such as a dial, provided outside the imager-system-position setting screen and for changing the tube position of the X-ray tube 11.

The CPU 20 determines whether to prepare for a transmission mode depending upon whether a line-of-sight direction determining operation or a line-of-sight direction changing operation is made on the FIG. 1 input device 28 (step S5). For example, the CPU 20 determines whether to prepare for a transmission mode depending upon whether the button "Set" is clicked on the imager-system-position setting screen shown in FIG. 4 or the button "Display 3D Image" is clicked after moving the imager-system virtual position.

When the determination at the step S5 is Yes, i.e. when a line-of-sight direction determining operation is done on the input device 28 and the CPU 20 determines a preparation for a transmission mode, the CPU 20 controls the couch driver 42 and gantry driver 43 to automatically align the couch plate 12 and gantry 14, as the imager system, in a manner to obtain a transmission image in the same image-taking direction as the predetermined line-of-sight direction of the 3D image displayed at the step S4 (step S6). For example, when the button "Set" is clicked on the imager-system-position setting screen shown in FIG. 4, the CPU 20 controls the couch driver 42 and gantry driver 43 to automatically align the couch plate 12 and gantry 14 to a real position corresponding to the imager-system virtual position taken upon clicking the button "Set".

Then, transmission radiography is conducted in a transmission mode (step S7), followed by performing diagnosis, IVR (interventional radiology), post-operation follow-up, etc. In the transmission mode, the CPU 20 controls the high-voltage generator 41 to apply a high voltage to the X-ray tube 11 under the condition of a tube voltage and current suited for transmission radiography, e.g. 120 kV, 100 mA. Furthermore, the CPU 20 aligns the gantry 14 to a start point where to take a transmission image in the same image-taking direction as the predetermined line-of-sight direction of the 3D image displayed at the step S4. The CPU 20 controls the gantry driver 43 to rotate the gantry 14 forward or reverse a predetermined angle a time from the start point.

X-rays are irradiated from the X-ray tube 11 toward the patient P. The X-rays, irradiated from the X-ray tube 11, is shaped by a collimator (not shown) into the size of an X-ray incident surface of the X-ray detector 13.

In the transmission-image generator 36, a transmission image is generated from the output of the X-ray detector 13. Here, receiving data from the X-ray detector 13, the transmission-image generator 36 performs a processing of re-projection onto a plane orthogonal to an X-ray path connecting between the X-ray source of the X-ray tube 11 and the X-ray detector 13 or onto a plane parallel therewith, thereby generating a transmission image. The transmission image is displayed on the transmission-image monitor 27b of the display 27 through the display control 37 (step S8). Accordingly, at the step S8, a transmission image can be displayed that is obtained as to the same image-taking direction as the predetermined line-of-sight direction of the 3D image displayed at the step S4.

Meanwhile, when the determination at the step S5 is No, i.e. when a line-of-sight direction changing operation is done on the input device 28 and the CPU 20 determines not to make a preparation for a transmission mode, three-dimensional image processing is performed on the three-dimensional image data having a post-change line-of-sight direction, as information attached, of the three-dimensional image data stored by the image-data storage device 35 in conjunction with the line-of-sight direction changing operation, thereby generating 3D image data. The 3D image data is displayed as a 3D image on the 3D image monitor 27a (step S9). For example, when the image-system virtual position is moved on the imager-system-position setting screen of the FIG. 4 and then the button "Display 3D Image" is clicked, three-dimensional image processing is performed on the three-dimensional image data having a post-change imager-system virtual position, as information attached, of the three-dimensional image data stored by the image-data storage device 35, thereby generating 3D image data. The 3D image data is displayed as a 3D image on the 3D image monitor 27a. Then, returning to the step S5, the CPU 20 determines whether to or not to make a preparation for a transmission mode.

Incidentally, the line-of-sight direction determining or changing operation, using the input device 28, is not limited to the execution on the imager-system-position setting screen shown in FIG. 4 but can be made, say, on the screen of the 3D image monitor 27a where displaying the 3D image. When to perform a line-of-sight direction changing operation on the screen, the operator makes a dragging or so by using the input device 28. When performing a line-of-sight direction changing operation, a generation processing is properly made of three-dimensional image data having attached information of a post-change line-of-direction nearly in real time in conjunction with the line-of-sight direction changing operation. Then, the 3D image, as to the line-of-sight direction operated changed, is properly displayed on the 3D image monitor 27d. However, in the CT mode, 3D images in various line-of-sight directions are obtained by image-processing the collected projection data whereas, in the transmission mode, all the transmission images in image-taking directions corresponding to the 3D images in various line-of-sight directions cannot be obtained because of the mechanical restrictions to the imager system. For this reason, on the screen where displaying a 3D image, line-of-sight direction changing operation is enabled limitedly to the image-taking directions in a range where images or transmission images are obtainable.

Meanwhile, when to perform a line-of-sight changing operation on the screen of the 3D image monitor 27a displaying a 3D image, a direction may be determined to take an image of a sectional plane orthogonal to a direction designated by using the 3D image, e.g. blood-vessel extending direction, so that change can be made taking the relevant direction as a line-of-sight direction. Then, a generation process is made of three-dimensional image data having, as attached information, the post-change line-of-sight direction. The 3D image, as to a line-of-sight direction operated changed, is displayed on the 3D image monitor 27a. The blood-vessel extending direction may be automatically set up by an image processing based on a 3D image or manually established by an operator's designation of three points to the displayed 3D image, such as an MIP image.

Figure 5:
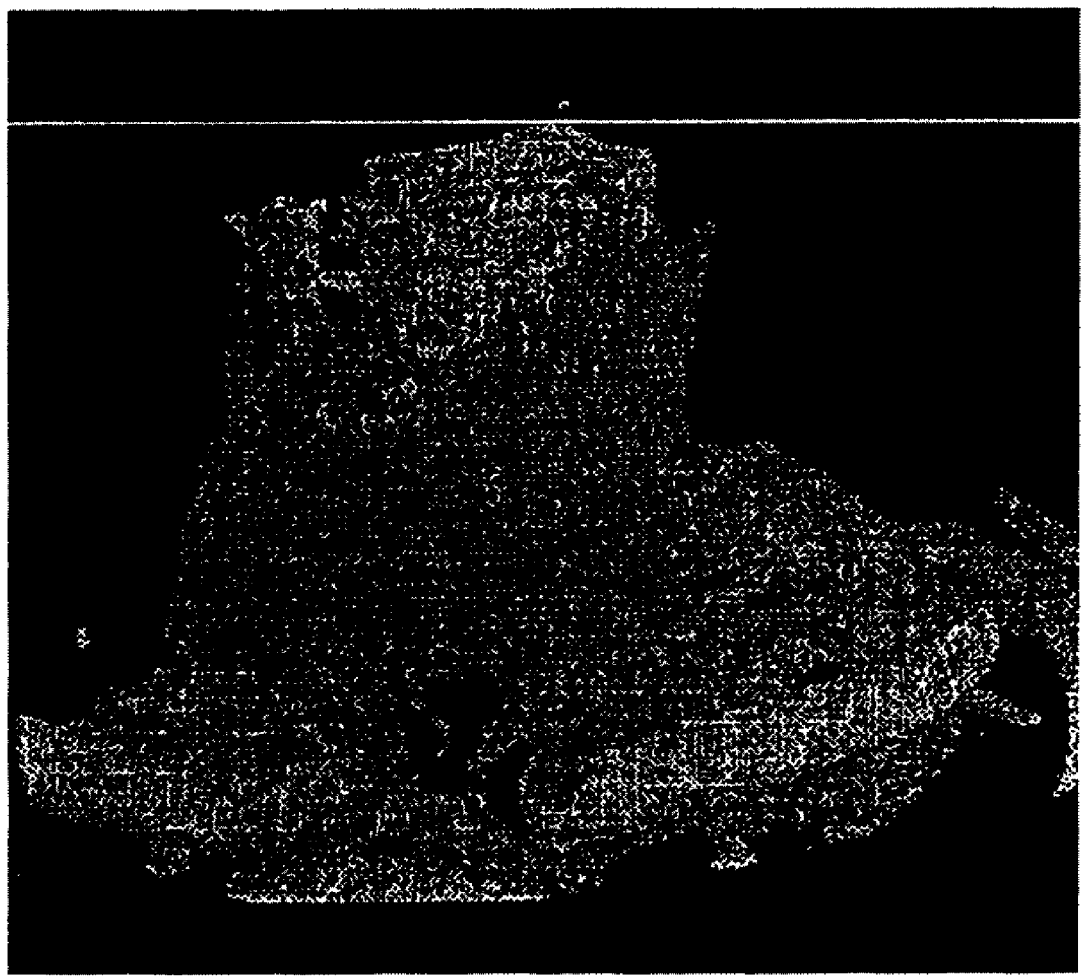
FIG. 5 is a figure showing an example of a 3D image displayed on the 3D image monitor.

FIG. 5 is a figure showing an example of a 3D image displayed on the 3D image monitor 27a. This 3D image is taken at the neck of the patient P, and different in line-of-sight direction from that shown in FIG. 3.

Figure 6:
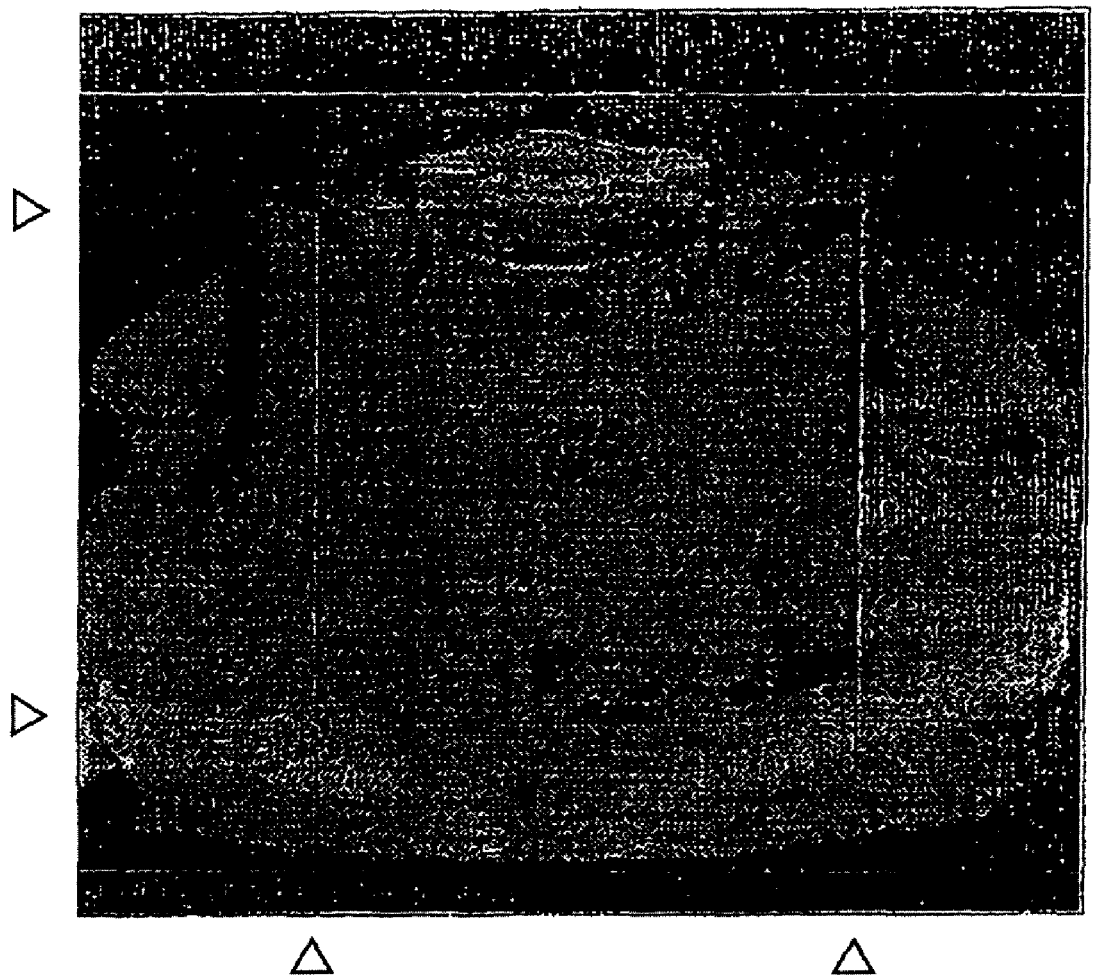
FIG. 6 is a figure showing a screen for regulating an opening degree of a collimator.

Incidentally, although the X-ray CT apparatus 10 has a collimator (not shown) to restrict the directivity (channel and slice directions) of the X-rays entering the X-ray detector 13, the collimator may be regulated in its virtual opening degree (on-screen opening degree of the collimator) on the 3D image displayed at the step S4, as shown in FIG. 6. In accordance with the virtual opening degree of the collimator regulated on the 3D image, an opening degree is determined for the real collimator, to take an image of a transmission image.

With the X-ray CT apparatus 10 and X-ray radiographic method in the present embodiment, a transmission image can be generated/displayed in the same image-taking direction as the line-of-sight direction of the 3D image generated/displayed in the CT mode. This eliminates the need of expose the patient P to X-ray radiation in a transmission mode during positioning the patient P, which reduces the patient P of exposure to X-ray radiation.

Figure 7:
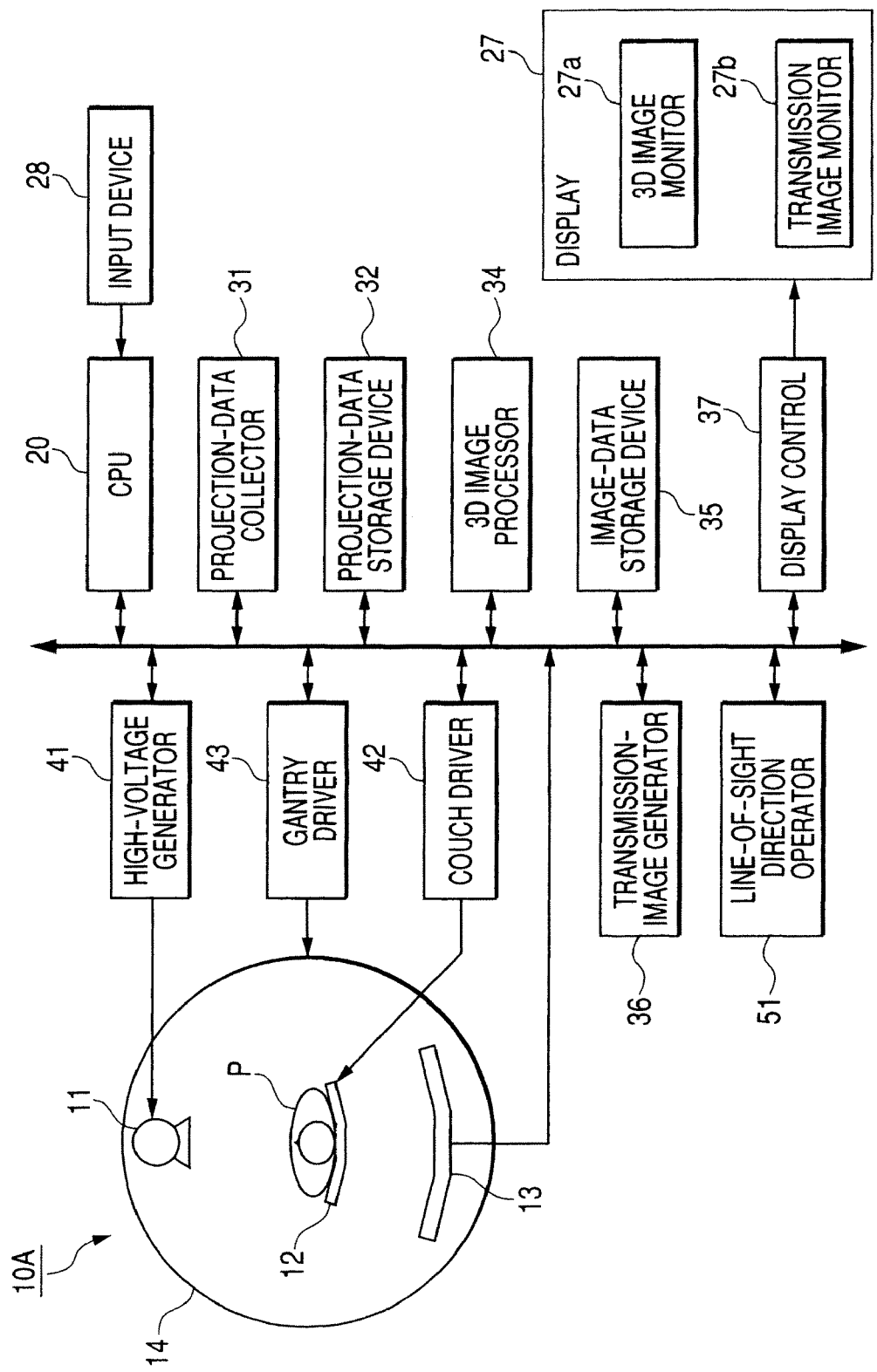
FIG. 7 is a schematic diagram showing a second embodiment of an X-ray CT apparatus according to the present invention.

FIG. 7 is a schematic diagram showing a second embodiment of an X-ray CT apparatus according to the invention.

In FIG. 7, there is shown an X-ray CT apparatus 10A. In the X-ray CT apparatus 1A, when the operator desirably designates a predetermined portion of a 3D image, the computer causes a CPU 20 to execute a program functioning as a line-of-sight direction operator 51 that operates a line-of-sight direction where to display a predetermined portion with magnification. Incidentally, in the X-ray CT apparatus 10A shown in FIG. 7, the same elements to those of the X-ray CT apparatus 10 shown in FIG. 1 are attached with the same reference numerals and explanation thereof is omitted.

Figure 8:
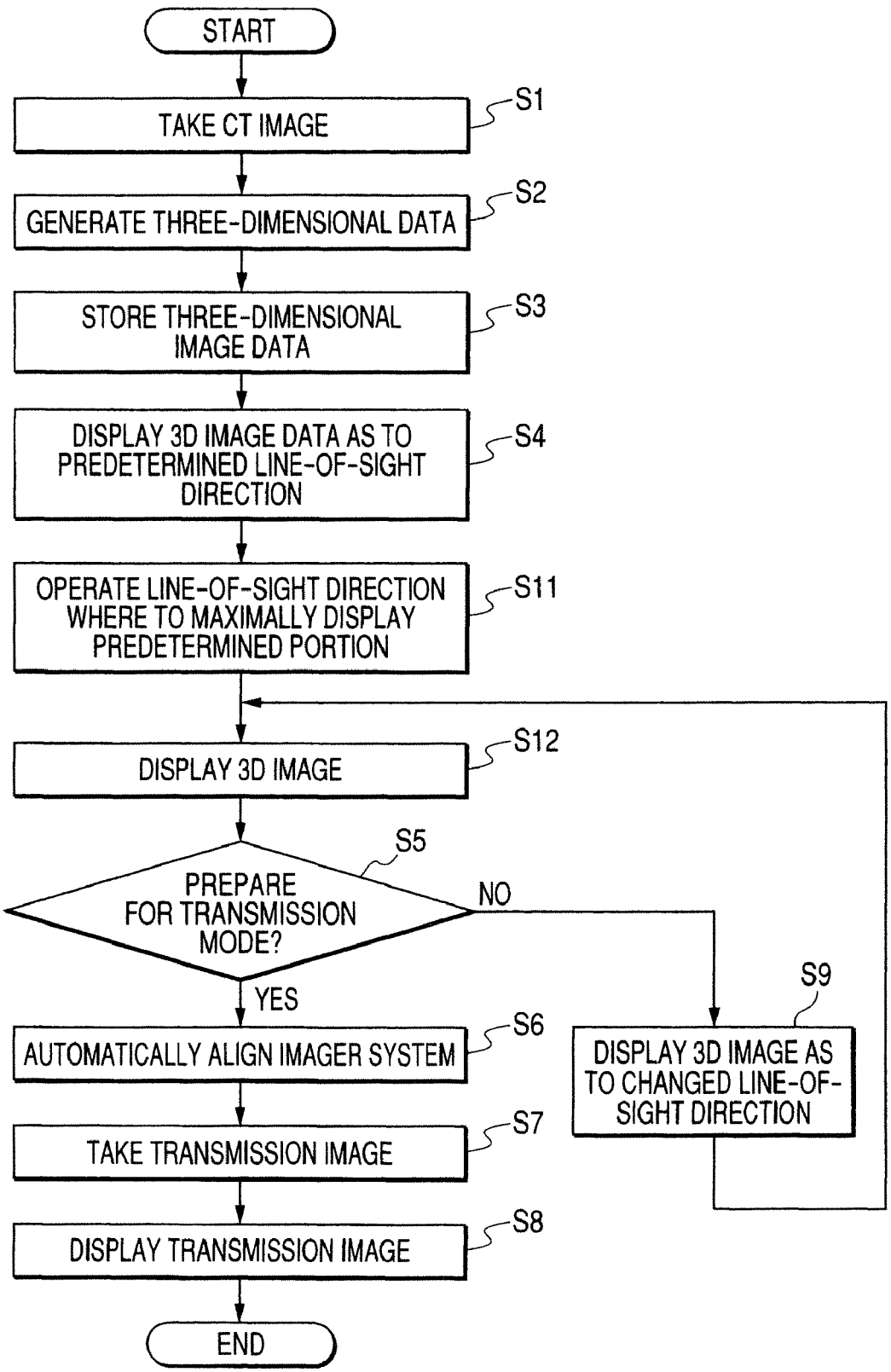
FIG. 8 is a flowchart of an X-ray radiographic method using the second embodiment of the X-ray CT apparatus.

Using a flowchart shown in FIG. 8, description is now made on an X-ray radiographic method using the X-ray CT apparatus 10A.

At first, CT imaging is performed in a CT mode on the patient P rested on a couch plate 12 for a diagnostic or remedial purpose (step S1), thus collecting projection data.

X-rays are irradiated from the X-ray tube 11 to the patient P. The X-rays in a portion transmitted the patient P are detected in amount by the X-ray detector 13. By the output of the X-ray detector 13, the projection-data collector 31 gathers the projection data as to the slice plane of the patient P. The projection data, gathered by the projection-data collector 31, is converted into a digital signal, which signal is stored in the memory by the projection-data storage device 32.

Based on the projection data gathered during the imaging at step S1 and stored by the projection-data storage device 32, the 3D image processor 34 generates three-dimensional image data in a plurality of line-of-sight directions (step S2). The 3D image data, generated by the 3D image processor 34, is each stored in the memory by the image-data storage device 35 (step S3).

Of the three-dimensional image data stored by the image data storage device 35, three-dimensional image data in a predetermined line-of-sight direction is image-processed three-dimensionally. Through the display control 37, the 3D image data is displayed as a 3D image on the 3D image monitor 27a of the display 27 (step S4).

Using the input device 28, the operator designates a predetermined portion out of the 3D image displayed at the step S4. The line-of-sight direction operator 51 operates a line-of-sight direction to display, with magnification, the predetermine portion desirably designated by the operator (step S11). For example, when a blood vessel part is designated in the 3D image by using the input device 28, the line-of-sight direction operator 51 operates a line-of-sight direction where the blood vessel part is displayed maximum on the 3D image.

The 3D image data, in a line-of-sight direction operated at the Step S11, is displayed as a 3D image on the 3D image monitor 27a through the display control 37 (step S12).

Then, the operator, who is to take an image of the patient P in a transmission mode, determines whether to display a transmission image of the neck in the same image-taking direction as the line-of-sight direction displayed at step S12 or to display a transmission image of the neck in an image-taking direction different from the line-of-sight direction displayed at step S12. Where desired to display a transmission image of the neck in the same image-taking direction as the line-of-sight direction displayed at the step S12, the operator performs a line-of-sight determining operation by use of the input device 28. Meanwhile, where desired to display a transmission image of the neck in an image-taking direction different from the line-of-sight direction displayed at the step S12, the operator performs a line-of-sight changing operation by use of the input device 28.

Depending upon whether a line-of-sight determining operation or a line-of-sight changing operation is done on the input device 28, the CPU 20 determines whether to or not to make a preparation for a transmission mode (step S5).

When the determination at the step S5 is Yes, i.e. when a line-of-sight direction determining operation is done on the input device 28 and the CPU 20 determines a preparation for a transmission mode, the CPU 20 controls the couch driver 42 and gantry driver 43 to automatically align the couch plate 12 and gantry 14, or imager system, in a manner to obtain a transmission image in the same image-taking direction as the line-of-sight direction of the 3D image displayed at the step S12 (step S6).

Then, transmission radiography is conducted in a transmission mode (step S7), followed by performing diagnosis, IVR (interventional radiology), post-operation follow-up, etc.

X-rays are irradiated from the X-ray tube 11 to the patient P. The X-rays, irradiated from the X-ray tube 11, is shaped by a collimator (not shown) into the size of an X-ray incident surface of the X-ray detector 13.

In the transmission-image generator 36, a transmission image is generated from the output of the X-ray detector 13. Here, receiving data from the X-ray detector 13, the transmission-image generator 36 performs a processing of re-projection onto a plane orthogonal to an X-ray path connecting between the X-ray source of the X-ray tube 11 and the X-ray detector 13 or onto a plane parallel therewith, thereby generating a transmission image. The transmission image is displayed on the transmission-image monitor 27b of the display 27 through the display control 37 (step S8). Accordingly, at the step S8, a transmission image can be displayed that is obtained in the same image-taking direction as the line-of-sight direction of the 3D image displayed at the step S12.

Meanwhile, when the determination at the step S5 is No, i.e. when a line-of-sight direction changing operation is done on the input device 28 and the CPU 20 determines not to make a preparation for a transmission mode, an image processing is performed three-dimensionally on the three-dimensional image data having information attached of a post-change line-of-sight direction, of the three-dimensional image data stored by the image-data storage device 35, thereby displaying the 3D image data as a 3D image on the 3D image monitor 27a (step S9).

Incidentally, although the X-ray CT apparatus 10A has the collimator (not shown) to restrict the directivity (channel and slice directions) of the X-rays entering the X-ray detector 13, the collimator may be regulated in its virtual opening degree on the 3D image displayed at the step S4 or S12, as shown in FIG. 6. In accordance with the virtual opening degree of the collimator regulated on the 3D image, a real opening degree is determined for the collimator, to take an image of a transmission image.

With the X-ray CT apparatus 10A and X-ray radiographic method in the present embodiment, a transmission image can be generated/displayed in the same image-taking direction as the line-of-sight direction of the 3D image generated/displayed in the CT mode. In the transmission mode, there is no need to expose the patient P to X-ray radiation during positioning the patient P, which reduces the patient P of exposure to X-ray radiation.

What is claimed is:

1. An X-ray CT apparatus comprising:
    an imager system configured to include a table-top and gantry which has at least an X-ray tube and a multi-slice detector;
    an input device configured to input a line-of-sight direction;
    a mode setter configured to set a mode in a CT mode;

a tomographic image generator configured to perform a tomographic imaging of a subject in which X-rays forming a cone beam are irradiated from the X-ray tube to the multi-slice detector, and to generate tomographic images based upon the tomographic imaging;

an image data storage device configured to store image data based upon the tomographic images;

a three-dimensional image processor configured to perform three-dimensional image processing on the image data and to generate a three-dimensional image, for display, corresponding to an input line-of-sight direction;

a mode switcher configured to switch the mode only between a transmission mode and the CT mode;

a drive controller configured to control an alignment of an imager system depending upon an image-taking direction corresponding to the line-of-sight direction;

a transmission image generator configured to perform a transmission imaging of the subject in which the X-rays are irradiated from the X-ray tube aligned by the drive controller to the multi-slice detector aligned by the drive controller, and to generate a transmission image, based upon the transmission imaging, in the image-taking direction corresponding to the line-of-sight direction of the displayed three-dimensional image generated by the CT mode; and a transmission image displayer configured to display the transmission image in substantially real-time.

2. The X-ray CT apparatus according to claim 1, further comprising:

an input device that inputs a predetermined portion of the three-dimensional image; and a line-of-sight direction operator that operates a line-of-sight direction to display the predetermined portion with magnification, thereby inputting the line-of-sight direction to the drive control.

3. The X-ray CT apparatus according to claim 1, further comprising:

a display control that causes display of, as a three-dimensional image, three-dimensional image data for display in the image-taking direction; and a monitor that displays the three-dimensional image.

4. The X-ray CT apparatus according to claim 1, further comprising:

a display control that causes display of the transmission image; and a monitor that displays the transmission image.

5. The X-ray CT apparatus according to claim 1, wherein the multi-slice detector includes a plurality of arrays each of which has a plurality of X-ray detecting elements matched to a spread of the X-ray cone beam.

6. An X-ray CT apparatus comprising:

an imager system configured to include a table-top and a gantry which has at least an X-ray tube and a multi-slice detector;

an input device configured to input a line-of-sight direction;

a mode setter configured to set a mode in CT mode;

a positioning device configured to input a tilt angle of the gantry and a tube position of the X-ray tube;

a drive controller configured to change the tilt angle and the tube position depending upon the tilt angle and tube position inputted by the positioning device;

a tomographic image generator configured to perform a tomographic imaging of a subject in which X-rays forming a cone beam are irradiated from the X-ray tube aligned by the drive controller to the multi-slice detector aligned by the drive controller, and to generate tomographic images based upon the tomographic imaging;

an image data storage device configured to store image data based upon the tomographic images;

a three-dimensional image processor configured to determine an image-taking direction depending upon the tilt angle and the tube position, to perform a three-dimensional image processing on the image data and to generate a three-dimensional image, for display, in a line-of-sight direction corresponding to the image-taking direction;

a mode switcher configured to switch the mode only between a transmission mode and the CT mode;

a transmission image generator configured to perform a transmission imaging of the subject in which the X-rays are irradiated from the aligned X-ray tube to the aligned multi-slice detector, and to generate a transmission image based upon the transmission imaging, in the image-taking direction, corresponding to the line-of-sight direction of the displayed three-dimensional image generated by the CT mode; and a transmission image displayer configured to display transmission image in substantially real-time.

7. The X-ray CT apparatus according to claim 6, wherein the positioning device is configured to input at least one of height, widthwise and longitudinal positions of a couch plate, the drive control being configured to determine a line-of-sight direction for the three-dimensional image processing depending upon at least one of the height, widthwise and longitudinal positions of the couch plate inputted by the positioning device.

8. The X-ray CT apparatus according to claim 6, wherein the three-dimensional image processor and the drive controller are configured to make a generation process of three-dimensional image data and to change the tilt angle and the tube position, in conjunction with an input to the input device.

9. The X-ray CT apparatus according to claim 6, wherein the multi-slice detector includes a plurality of arrays each of which has a plurality of X-ray detecting elements matched to a spread of the X-ray cone beam.

10. An X-ray radiographic method by using an imager system configured to include a table-top and a gantry which has at least an X-ray tube and a multi-slice detector, comprising:

mode setting to set a mode in a CT mode;

inputting a line-of-sight direction;

tomographic imaging performing to perform a tomographic imaging of a subject in which X-rays forming a cone beam are irradiated from the X-ray tube to the multi-slice detector;

tomographic image generating to generate tomographic images based upon the tomographic imaging;

image data storing to store image data based upon the tomographic images;

three-dimensional image processing to perform a three-dimensional image processing on the image data and to generate a three-dimensional image, for display, corresponding to a line-of-sight direction inputted;

mode switching to switch the mode only between a transmission mode and the CT mode;

drive controlling to control an alignment of an imager system depending upon an image-taking direction corresponding to the line-of-sight direction;

transmission image generating to perform transmission imaging of the subject in which the X-ray are irradiated from the X-ray tube aligned by the drive controlling to the multi-slice detector aligned by the drive controlling, and to generate a transmission image, based upon the transmission imaging, in the image-taking direction corresponding to the line-of-sight direction of the displayed three-dimensional image generated by the CT mode; and transmission image displaying to display the transmission image in substantially real-time.

11. The X-ray radiographic method according to claim 10, further comprising:

line-of-sight direction operating that, when establishing a predetermined portion of the three-dimensional image, operates in a line-of-sight direction to display the predetermined portion with magnification, whereby the drive control aligning is effected by inputting the line-of-sight direction.

12. The X-ray radiographic method according to claim 10, wherein the three-dimensional image processing uses at least one of a volume rendering process, a surface rendering process, a MPR (multi planar reconstruction) process, a CVR (computed volume radiography) process and a MIP (minimum intensity projection) process.

13. The X-ray radiographic method according to claim 10, wherein at least one of a tube position of an X-ray tube, a tilt angle of a gantry and a position of a couch plate is used as a position of the imager system.

14. The X-ray radiographic method according to claim 10, further comprising:

three-dimensional image displaying that displays, as a three-dimensional image, three-dimensional image data as to the line-of-sight direction.

15. The X-ray radiographic method according to claim 10, wherein a virtual opening degree of a collimator of the imager system is regulated on a three-dimensional image displayed in the three-dimensional image displaying, the opening degree of the collimator of the imager system being inputted according to the virtual opening degree after regulating to effect the drive controlling.

16. The X-ray radiographic method according to claim 14, wherein the three-dimensional image processing includes properly generating three-dimensional image data, for display, corresponding to a post-change line-of-sight direction in conjunction with a change of a line-of-sight direction done on a screen for establishing a position of the imager system.

17. The X-ray radiographic method according to claim 16, wherein the position of the imager system is established based on a numeral representative of a position of the imager system, on the screen.

18. The X-ray radiographic method according to claim 14, wherein the three-dimensional image processing includes properly generating three-dimensional image data, for display, corresponding to a post-change line-of-sight direction in conjunction with a change of a line-of-sight direction done on a screen of a three-dimensional image displayed in the three-dimensional image displaying.

19. The X-ray radiographic method according to claim 18, wherein the line-of-sight direction inputting is prohibited from establishing an image-taking direction when a transmission image cannot be acquired in the imager system.

20. The X-ray radiographic method according to claim 14, wherein three-dimensional image processing includes determining a line-of-sight direction for taking an image of a sectional plane orthogonal to a direction designated by using the three-dimensional image, on a screen of a three-dimensional image displayed in three-dimensional image displaying, and to generate three-dimensional image data, for display, corresponding to the line-of-sight direction.

21. The X-ray radiographic method according to claim 20, wherein the direction designated is taken as a blood vessel extending direction.

22. The X-ray radiographic method according to claim 10, further comprising:

transmission image displaying that displays the transmission image.

* * * * *